(12) United States Patent
Flanagan

(10) Patent No.: US 6,860,960 B1
(45) Date of Patent: Mar. 1, 2005

(54) METHOD OF APPLYING A LASER BEAM AROUND THE CIRCUMFERENCE OF A CATHETER

(75) Inventor: Aiden Flanagan, Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/654,987

(22) Filed: Sep. 5, 2000

(51) Int. Cl.[7] .............................................. B32B 31/28
(52) U.S. Cl. ............................. 156/272.8; 156/275.1; 156/290; 156/294; 156/308.4
(58) Field of Search .......................... 156/272.8, 275.1, 156/290, 294, 308.4

(56) References Cited

U.S. PATENT DOCUMENTS

| | | | |
|---|---|---|---|
| 3,957,339 A | | 5/1976 | Engel |
| 4,044,936 A | | 8/1977 | Obersby et al. |
| 4,251,305 A | | 2/1981 | Becker et al. |
| 4,456,811 A | | 6/1984 | Hella et al. |
| 4,623,776 A | * | 11/1986 | Buchroeder et al. ... 219/121.67 |
| 4,772,275 A | * | 9/1988 | Erlich ........................ 206/364 |
| 4,913,701 A | | 4/1990 | Tower |
| 4,943,278 A | | 7/1990 | Euteneuer et al. |
| 5,096,511 A | | 3/1992 | Fetting |
| 5,208,434 A | | 5/1993 | Minamida et al. |
| 5,339,380 A | * | 8/1994 | Wysocki et al. ............ 385/136 |
| 5,501,759 A | | 3/1996 | Forman |
| 5,506,702 A | | 4/1996 | Simpson |
| 5,595,670 A | * | 1/1997 | Mombo-Caristan .... 219/121.64 |
| 5,781,317 A | | 7/1998 | Kawazoe et al. |
| 5,957,930 A | | 9/1999 | Vrba |
| 6,010,521 A | | 1/2000 | Lee et al. |
| 6,027,477 A | | 2/2000 | Kastenhofer |
| 6,068,634 A | | 5/2000 | Lorentzen Cornelius et al. |

FOREIGN PATENT DOCUMENTS

| | | |
|---|---|---|
| DE | 1 479 239 | 6/1969 |
| NL | 1008178 | 10/1999 |
| WO | 97/32624 | 9/1997 |

OTHER PUBLICATIONS

U.S. patent application Ser. No. 09/427,805, Wang et al., filed Oct. 27, 1999.
U.S. patent application Ser. No. 08/926,905, Wang et al., filed Sep. 10, 1997.
U.S. patent application Ser. No. 09/407,836, Wang et al., filed Sep. 28, 1999.

\* cited by examiner

Primary Examiner—Sam Chuan Yao
(74) Attorney, Agent, or Firm—Mayer Portkort & Williams, PC; Stuart E. Mayer, Esq.

(57) ABSTRACT

A polymeric material may be bonded to a polymeric catheter tube by generating at least one annular beam of electromagnetic energy at a wavelength that is at least partially absorbed by at least one of the polymeric material and the polymeric catheter tube, controllably directing the annular beam of energy onto the polymeric material to concentrate the energy in a bond site circumscribing the catheter tube to at least partially melt at least one material selected from the group consisting of the polymeric material and the polymeric catheter tube along the bond site and the immediate region thereof and allowing the at least one partially melted polymeric material to cool and solidify to form a fusion bond between the tube and the polymeric material.

21 Claims, 11 Drawing Sheets

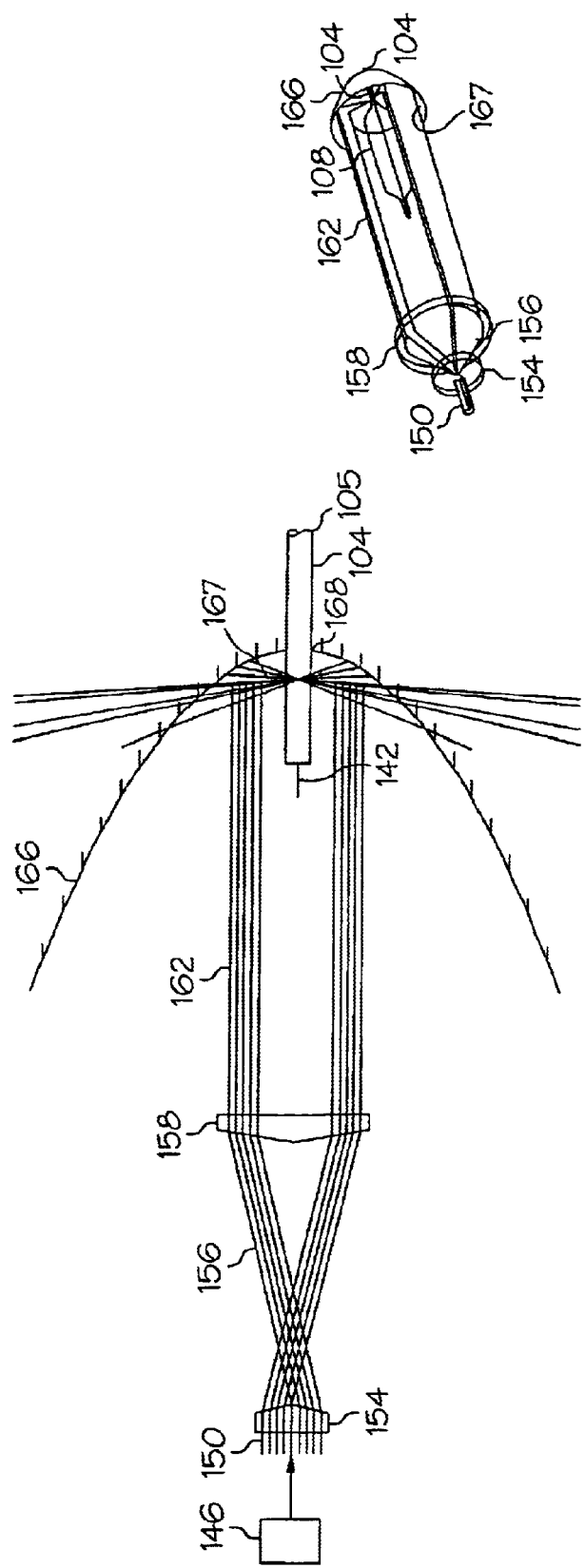

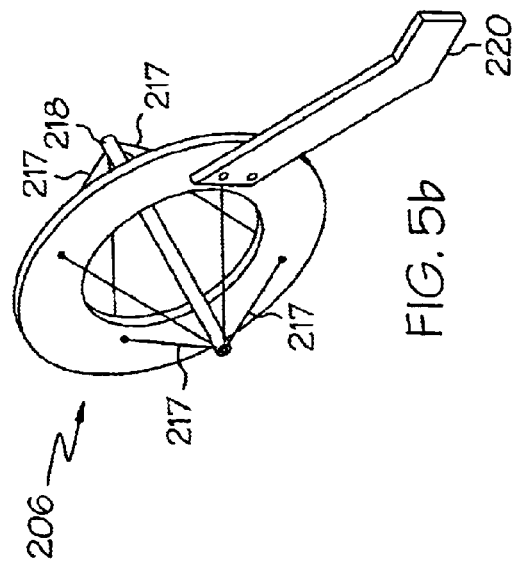
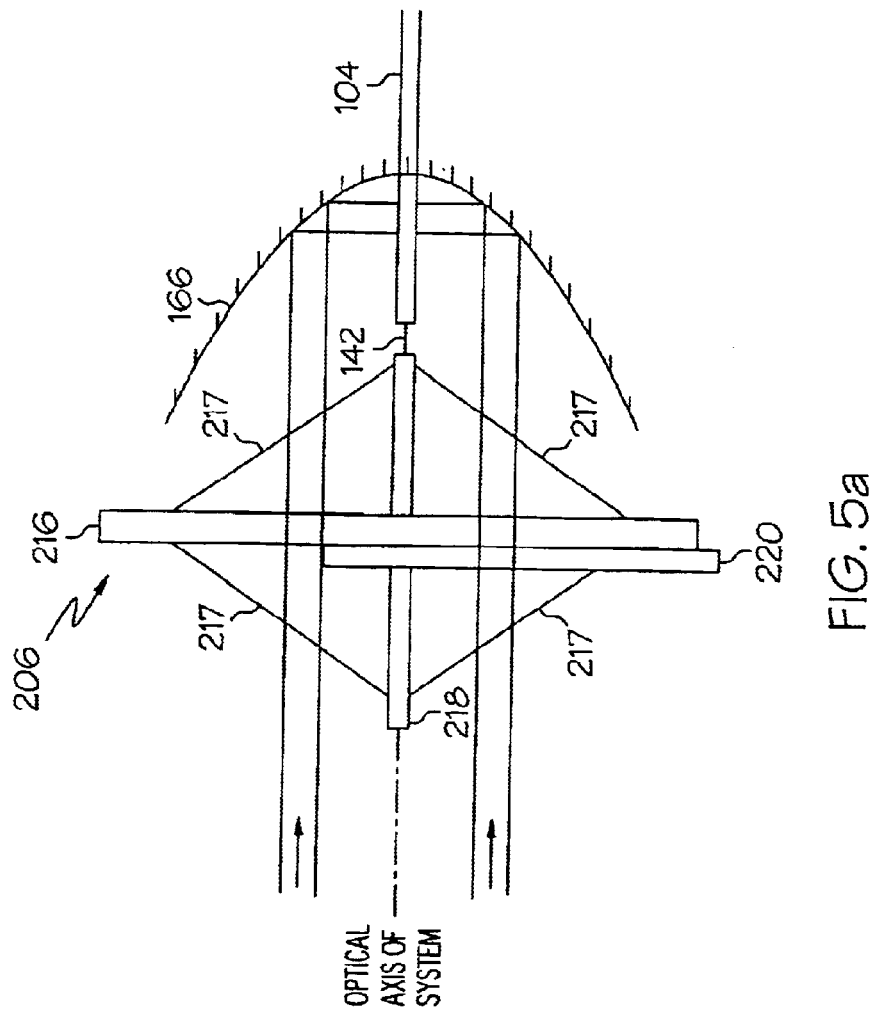

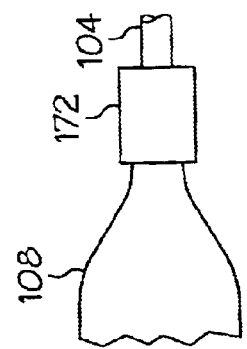
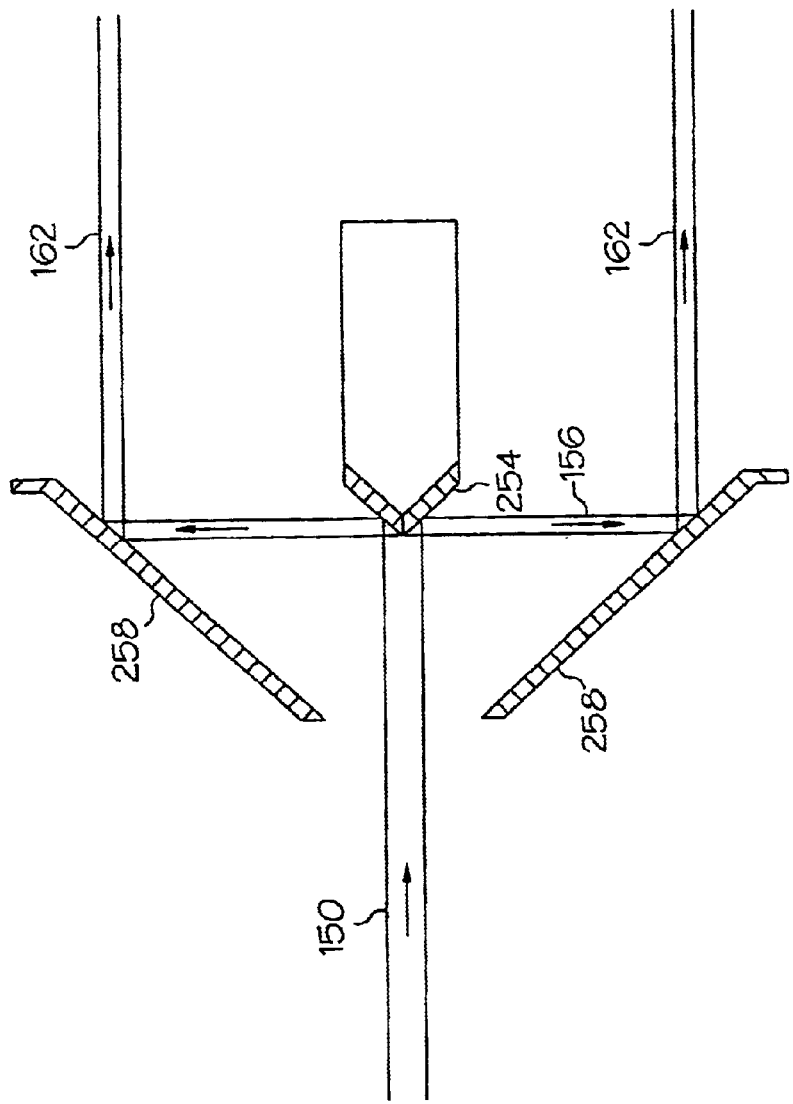
FIG. 9
FIG. 8

METHOD OF APPLYING A LASER BEAM AROUND THE CIRCUMFERENCE OF A CATHETER

BACKGROUND OF THE INVENTION

Medical catheters having a balloon mounted thereon are useful in a variety of medical procedures. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure is supplied to the balloon through an inflation lumen in the catheter, thereby expanding the balloon.

It is essential in the manufacture of balloon catheters to properly seal the balloon to the catheter. The seal must be able to withstand the high pressures to which it is subjected on inflation of the balloon. A poor seal may result in leakage of inflation fluid and inability to achieve the desired pressure or even rapid loss of pressure and deflation of the balloon.

A number of methods for sealing a balloon to a catheter are known in the art. One such method involves the use of a suitable adhesive to bond the balloon to the catheter tube as disclosed, inter alia, in U.S. Pat. No. 4,913,701 to Tower and U.S. Pat. No. 4,943,278 to Euteneuer, et al. The use of adhesives, however, adds to the thickness of the catheter and increase its rigidity at the region of the bonds. Moreover, adhesive bonds are known to be generally inferior to fusion bonds.

Another such method, where heat fusible materials are employed, involves the application of heat to fuse the balloon to the catheter tube. To that end, resistance heating of copper jaws has been employed to fuse a balloon to a catheter tube. Resistance heating, however, is known to result in the formation of small, random channels at the balloon-catheter interface, giving rise to undesirable variations in the strength of different bonds. The heat also causes undesirable crystallization and stiffening of the balloon and catheter material, not only at the bond site, but also in both directions axially of the bond, due to heat conduction through the balloon and the catheter, and heat radiation from the jaws.

A non-contact method for heat sealing a balloon onto a catheter is disclosed in U.S. Pat. No. 4,251,305 to Becker et al. A length of thin tubing is slid over an elongated shaft of the catheter and shrink tubing installed over the thin walled tubing at its ends overlapping the catheter shaft. The shrink tubing is partially shrunk. Lamps emitting energy along the visible and infrared spectra are used to provide radiant energy to form gradually tapering thermoplastic joints that bond the tubing and shaft. This method, nevertheless, suffers from the problem of undesired heat transfer along the catheter and balloon.

Yet another fusion-based method disclosed in U.S. Pat. No. 5,501,759 to Forman involves the use of a beam of laser radiation at a wavelength selected to at least approximately match a wavelength of maximum spectral absorption of the polymeric materials forming the balloon member and body. The polymeric materials are melted by the radiation and then allowed to cool and solidify to form a fusion bond between the catheter tube and the balloon. In order to bond the balloon about its entire circumference to the catheter tube, the catheter tube may be rotated relative to the laser beam or the laser beam may be rotated relative to the catheter tube.

In the former case, rotation speeds of 400 rpm or higher are necessary to ensure even heating of the catheter tube and balloon material. Care must be taken, however, to avoid damaging the catheter during rotation. Where a stent is mounted on the balloon, rotation of the catheter is even more difficult because of issues of stent securement. Moreover, the process can be slow because of the time required for the motor to attain the desired speed.

In the latter case, rotation of the beam relative to the catheter may be effected via the use of mirrors and focusing lenses. Alignment is difficult to achieve and maintain in such a system because of vibration from moving parts. The process is slow because of the time involved in loading and unloading the catheter and waiting for the rotational beam to reach the desired speed. Moreover, such an arrangement can be expensive to build.

Another fusion-based method disclosed in Forman involves the simultaneous use of multiple beams of energy to supply energy at discrete points about the circumference of the balloon and thereby heat the balloon. A single beam is split into multiple discrete beams and the multiple discrete beams directed about the circumference of the balloon via fiber optics.

For the purpose of this disclosure, all US patents and patent applications and all other publications referenced herein are incorporated herein by reference in their entirety.

The invention in various of its embodiment is summarized below. Additional details of the invention and/or additional embodiments of the invention may be found in the Detailed Description of the Invention below.

BRIEF SUMMARY OF THE INVENTION

The instant invention in some of its embodiments provides a novel process for sealing a polymeric balloon material to a polymeric catheter tube.

In one embodiment, the invention is directed to a process for sealing at least one polymeric material to a polymeric catheter tube. In accordance with the process, a polymeric material and a polymeric catheter tube are provided. A source of energy is also provided. At least one wavelength of energy that is at least partially absorbed by at least one of the polymeric material and the polymeric catheter tube is selected and at least one annular beam of electromagnetic energy generated at said selected energy wavelength. The annular beam of energy is controllably directed onto the polymeric material to concentrate the energy in a bond site circumscribing the catheter tube to at least partially melt at least one material selected from the group consisting of the polymeric material and the polymeric catheter tube along the bond site and the immediate region thereof. Both materials may be heated directly by the energy beam and/or the at least one melted material may melt adjoining materials by conduction/heat transfer. After cooling, the two materials have mixed and re-solidified to form a fusion bond between the tube and the polymeric material. Desirably, the polymeric material is a polymeric balloon material.

In another embodiment, the invention is directed to a process for forming a fluid tight seal between a polymeric body and a polymeric dilatation member surrounding the polymeric body. The method comprises the steps of positioning a dilatation member of polymeric material along and in surrounding relation to a body of polymeric material with the dilatation member and body aligned to place a first surface portion of the dilatation member and a second surface portion of the body in a contiguous and confronting relation. The polymeric materials forming the body and the dilatation member may have non-uniform energy absorption spectra that include high absorptivity wavelength bands. At least one of the high absorptivity wavelength bands of the polymeric material forming the body and at least one of the high absorptivity wavelength bands of the polymeric material forming the dilatation member overlap one another in at least one range of overlapping wavelengths. A monochromatic energy wavelength that is contained within at least one of the overlapping wavelength ranges is selected and an annular beam of substantially monochromatic electromagnetic energy generated at said selected monochromatic energy wavelength. The annular beam of substantially monochromatic energy is controllably directed onto the polymeric body and the dilatation member to concentrate the monochromatic energy in a narrow bond site circumscribing the body and running along the interface of the first and second surface portions to melt the polymeric materials along the bond site and the immediate region thereof. The previously melted polymeric material is then allowed to cool and solidify to form a fusion bond between the body and dilatation member.

In another embodiment, the invention is directed to a process for simultaneously bonding at least two polymeric materials to a catheter tube. The process comprises the steps of providing a catheter tube having at least a first predetermined bonding location and a second predetermined bonding location for bonding a polymeric material thereto, each bonding location having a polymeric material circumscribing the catheter tube at the bonding location. A first annular beam of electromagnetic energy that is at least partially absorbed by the polymeric material at the first bonding location and a second annular beam of electromagnetic energy that is at least partially absorbed by the polymeric material at the second bonding location are simultaneously generated. The first and second annular beams of energy are controllably directed onto the polymeric balloon material at the first and second predetermined bonding locations to concentrate the energy into the first and second predetermined bond sites circumscribing the catheter tube and to at least partially melt the polymeric balloon material along the bond sites and the immediate regions thereof. The previously melted polymeric materials in the first and second bonding locations are allowed to solidify to form fusion bonds between the catheter tube and the polymeric material at the first and second bonding locations.

In yet another embodiment, the invention is directed to a process for simultaneously welding the proximal and distal ends of a balloon made of polymeric material to a catheter tube. The process comprises the steps of generating a first annular beam of electromagnetic energy at a wavelength that is at least partially absorbed by the balloon and a second annular beam of electromagnetic energy at a wavelength that is at least partially absorbed by the balloon, controllably directing the first annular beam toward the proximal end of the balloon to concentrate the energy in a narrow bond site circumscribing the catheter tube and running along the interface of the catheter tube and the proximal end of the balloon thus to melt the polymeric materials along said bond site and the immediate region thereof, simultaneously controllably directing the second annular beam toward the distal end of the balloon to concentrate the energy in a narrow bond site circumscribing the catheter tube and running along the interface of the first and second surface portions, thus to melt the polymeric materials along the bond site and the immediate region thereof and allowing the previously melted polymeric material to cool and solidify to form a fusion bond between the catheter tube and the proximal and distal ends of the balloon.

In yet another embodiment, the invention is directed to a process for bonding at least one polymeric material to a polymeric catheter tube. The method comprises the steps of generating at least one annular beam of electromagnetic energy that is at least partially absorbed by at least one of the polymeric material and the polymeric catheter tube at said selected energy wavelength, controllably directing at least a portion of the annular beam of energy onto the polymeric material to concentrate the energy in a bond site circumscribing at least a portion of the polymeric catheter tube to at least partially melt at least one material selected from the group consisting of the polymeric material and the polymeric catheter tube along the bond site and the immediate region thereof and allowing the at least one partially melted polymeric material to cool and solidify to form a fusion bond between the polymeric catheter tube and the polymeric material.

A detailed description of the invention in its various embodiments is provided below.

BRIEF DESCRIPTION OF THE SEVERAL VIEWS OF THE DRAWING(S)

FIG. 3 is a schematic view of an apparatus employed in the inventive process;

FIG. 4 shows the evolution of the beam of FIG. 3 in three dimensions;

FIG. 5a is a schematic view of fixture for holding a catheter;

FIG. 5b is an isometric view of the fixture of FIG. 5a;

FIG. 5c is an end view of the fixture of FIG. 5a;

FIG. 8 is a schematic view of another apparatus that may be employed in the inventive process;

FIG. 9 is a schematic side elevational view of a balloon with heat shrink tubing disposed thereon;

FIG. 15b is an end view of the apparatus of FIG. 15a.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

As used herein, the term "annular" encompasses ringlike shapes including those with a circular periphery and those with a non-circular periphery. An example of the latter is a ring whose periphery is elliptical.

Figure 1:
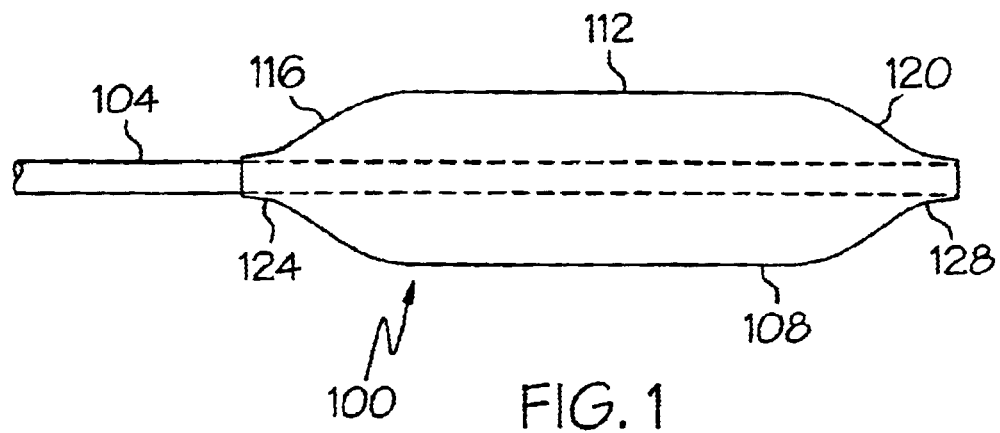
FIG. 1 shows a side elevational view of the distal end of a balloon catheter.

Turning to the drawings, the distal end region of a balloon catheter is shown generally at 100 in FIG. 1. The balloon catheter includes an elongate and pliable length of catheter tubing 104 constructed of a body compatible polymeric material such as a polyester. Desirably, a polyester such as Hytrel® may be used. Other suitable materials include polyolefins, polyamides and thermoplastic in polyurethanes, and copolymers of these materials. A balloon 108 surrounds catheter tubing 104 along the distal end region. The balloon is shown in its fully expanded configuration, as when the balloon contains a fluid, supplied under pressure to the balloon interior through a balloon inflation lumen (not shown) open to the proximal end of catheter tubing 104 and to the balloon interior.

Fully expanded, balloon 108 includes a main body region 112, disposed about catheter tubing 104, and with a diameter substantially larger than that of the tubing. The appropriate balloon and catheter tubing diameters vary, depending upon factors such as the size of the vessel or other body cavity, and the procedure involved. At opposite ends of main body region 112 are a proximal cone 116, and a distal cone 120. The proximal cone terminates in a proximal neck region 124. The inner diameter of neck region 124 is substantially equal to the outer diameter of catheter tubing 104 in the region of the proximal neck to provide an interface region along which the interior surface of neck region 124 and the exterior surface of catheter tubing 104 confront one another and are contiguous.

Distal cone 120 similarly terminates in a distal neck region 128. The distal neck also has an inner diameter substantially equal to the outer diameter of catheter tubing 104 in the region of the distal neck. Consequently, the diameter of distal neck 128 typically is less than the inner diameter of proximal neck 124 because the catheter tubing is narrower along the distal neck due to the termination of the balloon inflation lumen proximally of distal neck 128.

Dilatation balloon 108 is desirably made from made from PET (polyethylene terephthalate). Other suitable materials include polyethylene, polyvinyl chloride, Surlyn® polyethylene ionomer copolymer, Pebax® polyamide-polyether-polyester block copolymer, PBT (polybutylene terephthalate), poly(butylene terephthalate)-block-poly(tetramethylene oxide), Arnitel, Hytrel, polyetherether ketone (PEEK), Teflon, polytetrafluoro-ethylene (PTFE), nylon (for example, nylon 12), and their copolymers as well as other polyolefins and silicone elastomers. Other suitable balloon materials are disclosed in PCT publication WO 97/32624 and commonly assigned U.S. application Ser. No. 08/926905. More generally, suitable materials include a polymeric material that is sufficiently pliable or formable to readily achieve the enlarged configuration, yet is relatively inexpansible, tending to maintain the configuration shown in FIG. 1 under increased fluid pressure within the balloon. Of course, the material should be biocompatible.

Figure 2:
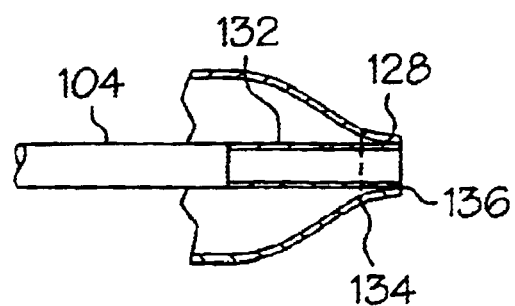
FIG. 2 shows an enlarged cross-sectional view of a portion of the balloon catheter of FIG. 1.

As shown in FIG. 2, catheter tubing 104 has a central lumen 132 to accommodate a guide wire (not shown) and, if desired, to provide a path for supplying drugs from the proximal end of the catheter tubing to a treatment site. A broken line at 134 indicates the proximal boundary of a fusion bond 136 between catheter tubing 104 and distal neck 128. Fusion bond 136 is annular, and is located along the interface between the distal neck and the catheter tubing. More particularly, the polymeric material along the inside surface of distal neck 128 and the polymeric material along the exterior surface of tubing 104 become fused and form the bond as they cool and solidify, to provide a fluid tight seal between the catheter tubing and the balloon.

Desirably, bond 136 has an axial dimension of at most 0.030 inches, and is within 0.030 inches of distal cone 120, for a length of the catheter distal tip (including distal neck 128 and the distal end of catheter tubing 104) of at most 0.060 inches. More desirably, the axial dimension of the bond is about 0.020 inches, and the bond is within 0.010 inches of cone 120. Further, the distal cone is substantially free of undesirable crystallization that results from thermal shock from the heat of bond formation.

In accordance with the present invention, fusion bonds between the catheter tubing and balloon are formed by a non-contact process, resulting in bonds that are much narrower yet withstand burst pressure to the same degree as conventional bonds. Moreover, as compared to conventionally formed bonds, bonds formed according to the present invention can be positioned substantially closer to the cones of the balloon, without the crystallization or attendant stiffening.

An apparatus used in forming the inventive balloon catheter is illustrated schematically in FIG. 3. Catheter tube 104 is disposed about mandril 142 formed of stainless steel or other suitable material. The outside diameter of mandril 142 is approximately equal to the inner diameter of catheter tube 104 so that the mandril receives catheter tubing 104 in sliding or slip fit fashion. Catheter tube 104 extends through hole 168 in parabolic mirror 166 and is positioned such that the desired bond region resides in the focal region of parabolic mirror 166.

Parabolic mirror 166 may also be split in half and provided in clam-shell like form, to facilitate positioning of the catheter.

A system for directing energy, desirably monochromatic energy, onto mandril 142, includes a laser source 146 which generates laser beam 150. Desirably, beam 150 will have a wavelength in the infrared range. More desirably, the laser is a $CO_2$ laser operating at a wavelength of about 10.6 microns. The invention also contemplates the use of lasers operating in the ultraviolet range. Other suitable lasers for use include diode lasers.

Beam 150, having a circular cross-section, is directed through a first conical lens 154 which forms a diverging annular beam 156. Annular beam 156 is directed through a second conical lens 158 which collimates the beam to produce a collimated annular beam 162. The collimated beam is then focused with parabolic mirror 166 into beam 167 which is directed onto the entire circumference of catheter 104 at the desired bond site. The focal size may be adjusted by varying the input diameter of the laser beam, the divergence angle of the first conical lens, the separation between the first and second lenses and the focal length of the parabolic mirror.

The evolution of the beam is shown in FIG. 4 from a three dimensional perspective.

The focal size and focal intensity may be varied by varying the input divergence angle of the laser or the focal length of the parabolic mirror.

Figure 5C:
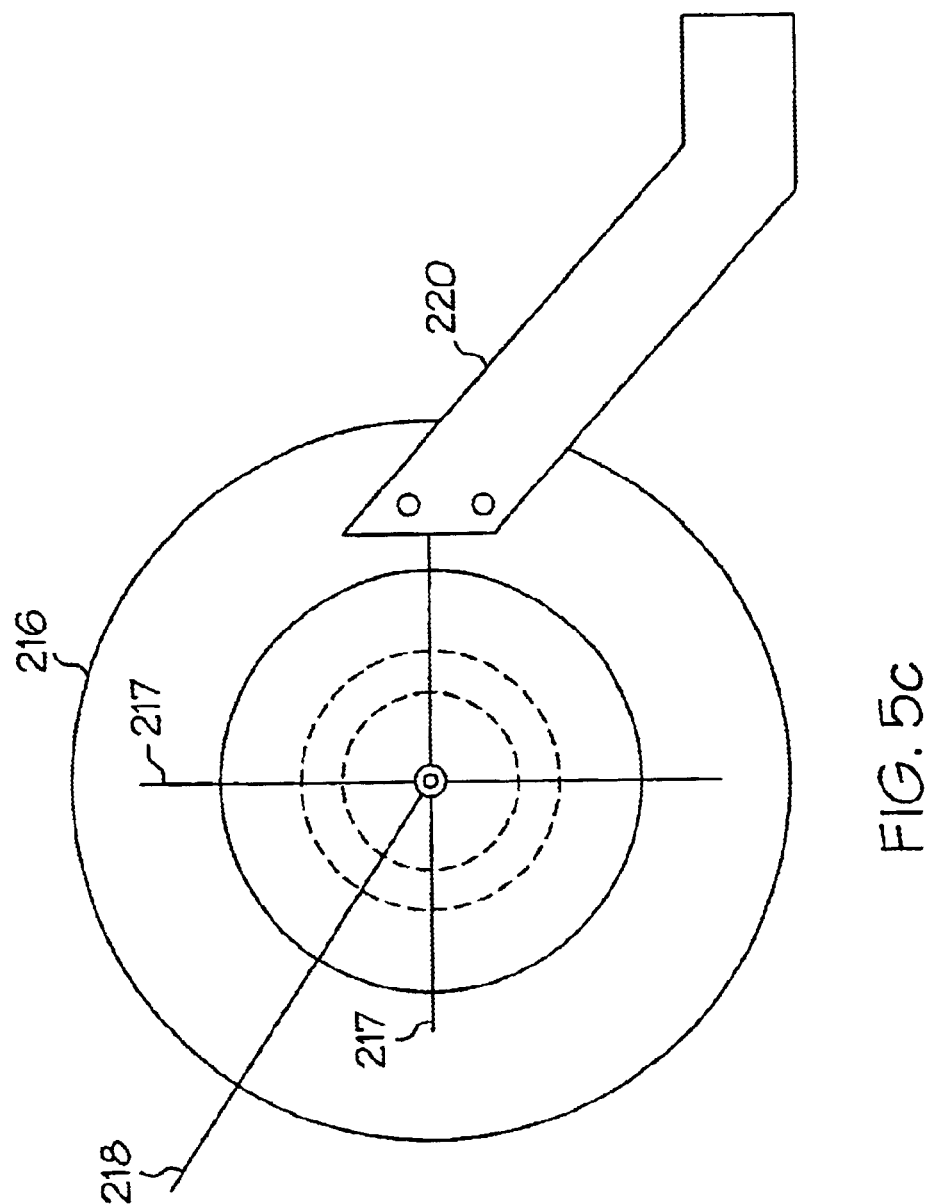

Distal end 105 of the catheter 104 may further be supported by a fixture held by wires which radiate from the optical axis through the annular beam and fixed in place externally as shown in FIGS. 5a–5c.

As shown in FIGS. 5a and 5b, a fixture, shown generally at 206, includes an annular portion 216 with a central support bar 218 extending therethrough. Central support bar 218 has an opening therein to accommodate a mandril 142 therein. The opening may optionally extend the length of the central support bar to accommodate a portion of a catheter therein. Central support bar 218 may be made of any suitable material including polymeric material or metal. Central support bar 218 is supported by three supports 217 extending from a first side of annular portion 216 and three supports 217 extending from a second side of annular portion 216. The supports may be made of wire or other rigid materials including metal and polymeric materials. Additional or fewer supports may also be provided. Annular portion 216 is, in turn, supported by support 220. Support 220 may be of any suitable shape which is capable of supporting fixture 206. Support 220 may optionally include clamps or other devices for holding fixture 206 in place. An isometric view of fixture 206 is provided in FIG. 5b and an end view of fixture 206 is provided in FIG. 5c.

Alternatively, the mandril may be supported by a suitable structure such as a wire fixture extending from one of the lenses.

Figure 5D:
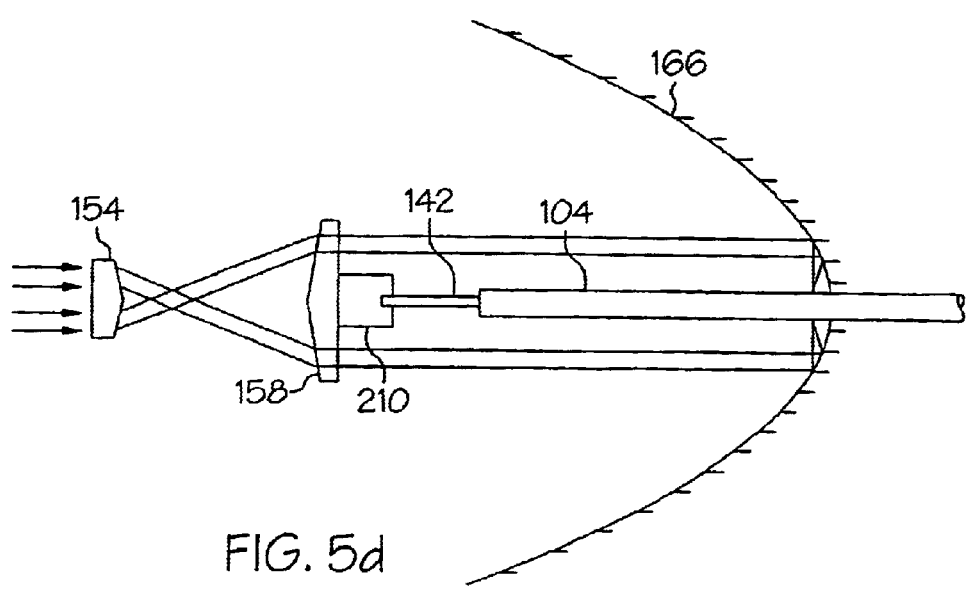
FIGS. 5d and 5e are schematic views of other fixtures for holding a catheter.

Another method of securing the distal end of the catheter is shown in FIG. 5d. Mandril 142 is held by fixture 210. Fixture 210 has an opening therein sized to receive mandril 142 therein. Fixture 210 may be attached to conical lens 158 through any suitable means including the use of an adhesive.

Figure 5E:
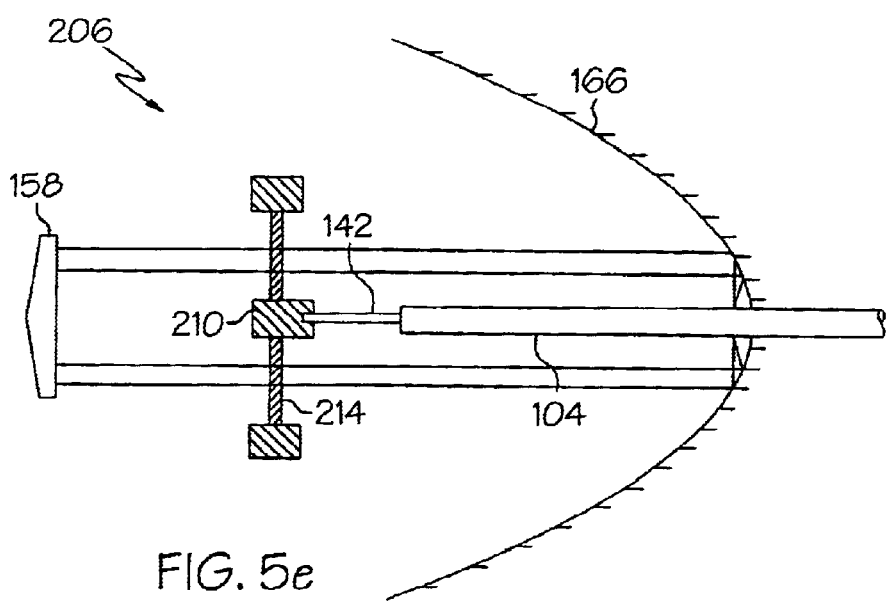
Figure 5F:
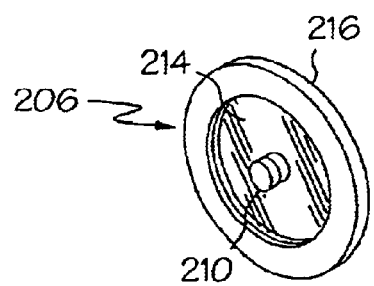
FIG. 5f is an isometric view of the fixture of FIG. 5e.

Yet another suitable arrangement is shown in FIGS. 5e and 5f. A fixture, shown generally at 206 includes a tip holder 210 for receiving mandril 142 therein. As shown in perspective in FIG. 5f, tip holder 210 is attached to the center of window 214. Window 214 is transparent to the laser radiation and placed between conical lens 158 and catheter 104. Window 214 is mounted to or otherwise secured to annular ring 216. Desirably, window 214 will be made of ZnSe.

Figure 7:
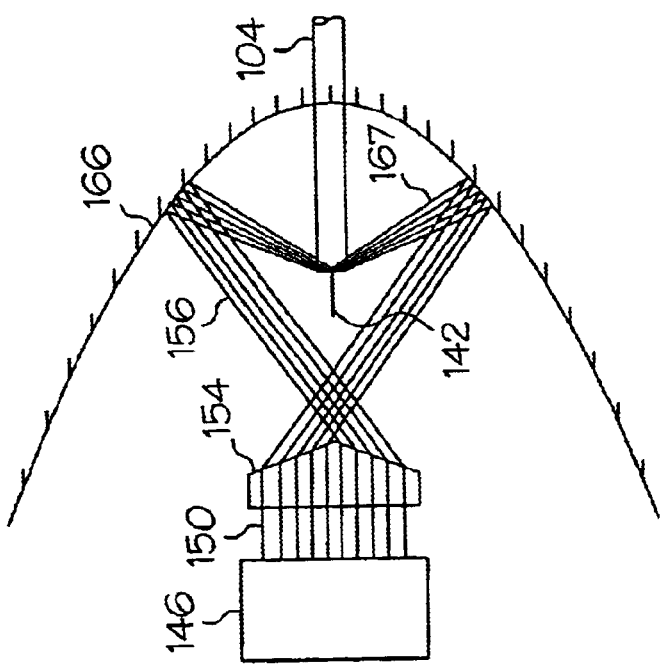
FIG. 7 is a schematic view of an apparatus similar to that of FIG. 6 with a larger focus beam.
Figure 6:
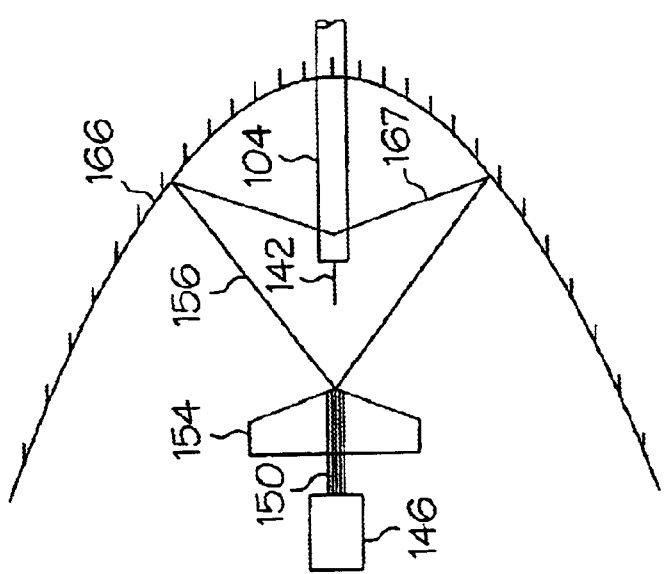
FIG. 6 is a schematic view of another apparatus that may be employed in the inventive process.

As shown in FIGS. 6 and 7, the inventive process may also be practiced using an apparatus similar to that shown in FIG. 3 without second conical lens 158. In this case, diverging annular beam 156 is redirected and refocused using parabolic mirror 166 into beam 167 which is directed onto the entire circumference of catheter 104 at the desired bond site. The focal size may be adjusted by varying the input diameter of the laser beam and/or the focal length of the parabolic mirror. FIG. 6 shows an embodiment with a small focus beam size. FIG. 7 shows an embodiment with a larger focus beam size.

The inventive process may also be carried out using the arrangement shown in FIG. 8. Laser beam 150 is directed at conical mirror 254. Reflected beam 156 is directed toward a second conical mirror 258 where it is collimated. Collimated beam 162, reflected off second mirror 258 is annular and may be redirected by a parabolic mirror (not shown) toward a catheter or balloon in accordance with the invention.

In accordance with the invention, a balloon catheter may be prepared by placing catheter tube 104 onto mandril 142. Optionally, a relatively short (0.25 inches) length of heat shrink tubing 172, desirably constructed of a polyolefin, my be disposed about catheter tube 104 as shown in FIG. 9 and suitably aligned. Balloon 108 is disposed about catheter tube 104 in a desired location. Where heat shrink tubing is employed, the portion of the balloon to be bonded to the catheter tube, typically the proximal and/or distal neck region, is inserted within heat shrink tubing 172. The balloon may also be positioned about the catheter first and the heat shrink tubing subsequently positioned over the desired portion of the balloon.

The region of the catheter and balloon assembly to be bonded is then placed within the focal region of parabolic mirror 166 or, more generally, depending on the particular arrangement of optical equipment, within the focused annular beam 167. For example, where the intended fusion bond width is 0.030 inches and the bond is to be spaced an axial distance of 0.010 inches from the distal cone, the laser system is such that beam 167 is aligned on the intended center of the bond relative to the distal cone, i.e. at 0.025 inches from the cone. The region to be bonded may also be held stationary and the laser and associated optics adjusted to provide a focused annular beam at the bond region.

Once catheter tube 104, balloon 108 and optional heat shrink tubing 172 are properly positioned, a laser beam 150 of required energy is generated by laser source 146 and shaped and focused, as discussed above, into annular beam 167 directed at the desired bond region, as shown in FIG. 3.

Figure 10:
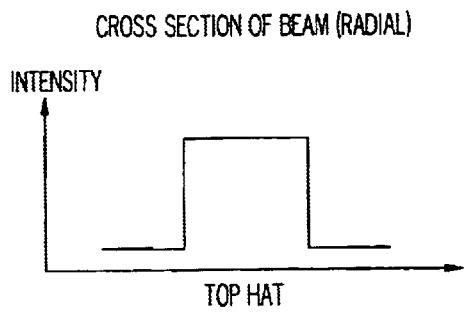
FIGS. 10 and 11 depict a substantially constant profile and a gaussian profile, respectively, of a laser beam with the intensity of the beam plotted as a function of location along the beam diameter.
Figure 11:
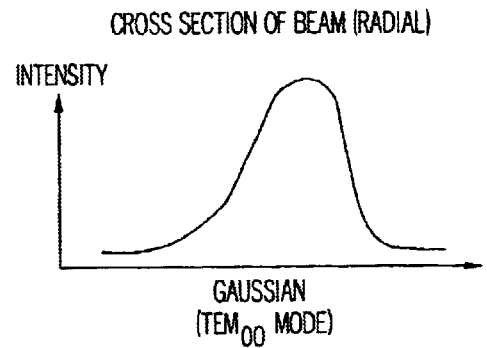

The concentration of energy necessary for fusion bonding at the bond site may be suitably controlled via several different parameters. First, the beam may be focused over a shorter or longer length of polymeric material. Where the beam is focused over a shorter length of polymeric material, the energy source may be operated at a lower wattage or for shorter duration. Second, where the energy source is a laser, the laser beam will desirably have a profile which is constant or substantially constant across the beam diameter as shown in FIG. 10 or a profile which is gaussian ($TEM_{00}$ mode) or substantially gaussian across the beam diameter as shown in FIG. 11. Third, the wavelength of the energy, desirably laser energy, and the polymeric materials of the balloon and catheter tubing will desirably be matched. That is, the polymeric materials being bonded together will desirably have a high absorptivity for energy at the selected wavelength (for example, 10.6 microns in the case of a $CO_2$ laser).

Information on the absorptivity of various materials, with respect to wavelength of the energy, is available, for example in *The Infrared Spectra* Atlas of Monomers and Polymers, published by Sadtler Research Laboratories. A more detailed discussion of the matching may be found in U.S. Pat. No. 5,501,759.

By suitably adjusting the focus of the beam and by providing energy at one or more wavelengths that are selected to be strongly absorbed by at least one and desirably both of polymeric materials, heat sufficient to fuse an outer surface of the catheter tubing and an inner surface of distal neck of the balloon may be generated at a laser power of less than 10 watts. A duration of about 0.5 seconds to about 3 seconds of laser energy application has been found satisfactory for forming bonds that can withstand burst pressures exceeding 400 pounds per square inch, and the degree of control over the laser yields a high degree of consistency among the bonds. Typically, the laser energy is applied continuously for a period of 1 to 2 seconds at a power level of 1 Watt. Desirably, the laser energy will be focused to an approximately 1 mm wide annulus on the balloon. After the fused material cools and solidifies, the heat shrink tubing if present is removed.

Because of the high absorptivity one or both of the polymeric materials at the chosen wavelength(s), there is no substantial conduction of heat along the mandril in either axial direction away from the bond site. Also, the heat conductivity of polymers is low and the laser is on for only a short period of time. Thus, there is no undue heating of portions of the tubing and balloon near the bond which would lead to crystallization and stiffening of the polymeric materials. As such, a distal bond can be positioned within 0.010 inches of the distal cone without any substantial crystallization or stiffening of the cone.

In another embodiment of the invention, a holographic optical element (HOE) or a diffractive element maybe used in place of the conical lens to form the annular beam.

HOE's are well known in the art. An HOE is formed by overlapping a reference laser beam and a modified laser beam. An HOE of a lens, for example, may be formed by mixing a reference laser beam with a converging laser beam at a holographic plate. Subsequently, when a laser beam identical to the reference beam is incident on the holographic plate, a converging beam emerges and the HOE behaves like a lens.

The HOE required for an emerging annular beam is formed by a similar method. A reference laser beam and a diverging annular laser beam (after passing through a conical lens) are directed so that they are incident and overlappings on the holographic plate. The developed hologram has the property that when the reference laser beam is incident thereon, the emerging laser beam is annular.

In yet another embodiment of the invention, an HOE, a diffractive element, a refractive element or reflecting element may be used to focus the annular beam around the circumference of the catheter. Examples of suitable elements include a circular, elliptical or hyperbolic mirror or lens.

Figure 12:
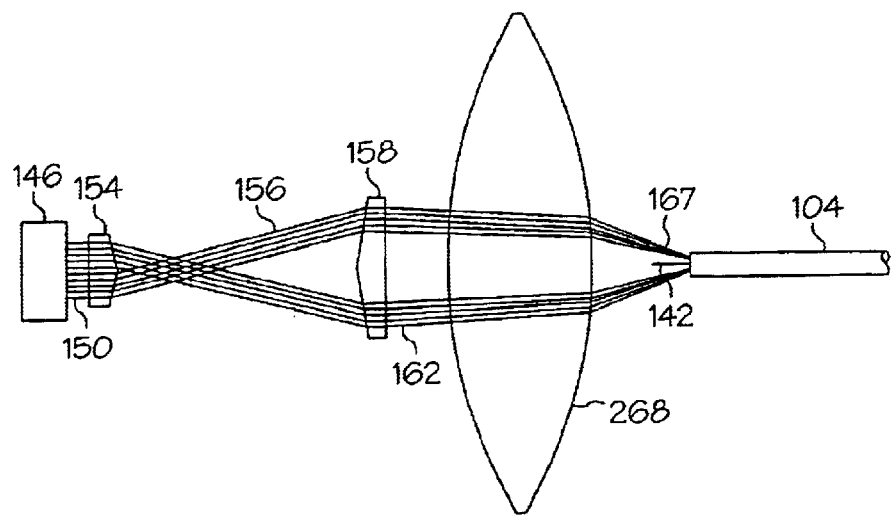
FIG. 12 is a schematic view of another apparatus that may be employed in the inventive process.

FIG. 12 illustrates the use of a refractive element in the practice of another inventive embodiment of the invention. Energy source 146, desirably a laser, generates beam 150 which is refocused via lens 154 into annular beam 156. Lens 158 collimates annular beam 156. Refractive lens 268 then focuses collimated beam 162 onto catheter 104.

The invention fuller contemplates simultaneously bonding multiple portions of a catheter. For example, both the proximal and distal ends of a balloon may be bonded to a catheter simultaneously. An HOE may be used to produce two or more annular beams which may then be focused to both the proximal end and the distal end of the balloon. An HOE for two or more annular beams is produced by multiple exposure of a holographic plate using different conical lenses with different conical angles. For example, for a two annular beam hologram the holographic plate is first exposed to an overlapping reference beam and a diverging beam from a conical lens of a first cone angle A. The holographic plate is then exposed to the same reference beam and a diverging beam from a different conical lens of a second cone angle B. After processing, the hologram will produce two diverging annular beams when illuminated with the reference beam.

The proximal and distal ends of the balloon may also be non-simultaneously bonded to a catheter using separate annular beams generated by an HOE. Two different HOE's are used to achieve this effect. The laser is directed to each one in turn. The same effect may also be achieved using a single HOE with two different areas.

Figure 13:
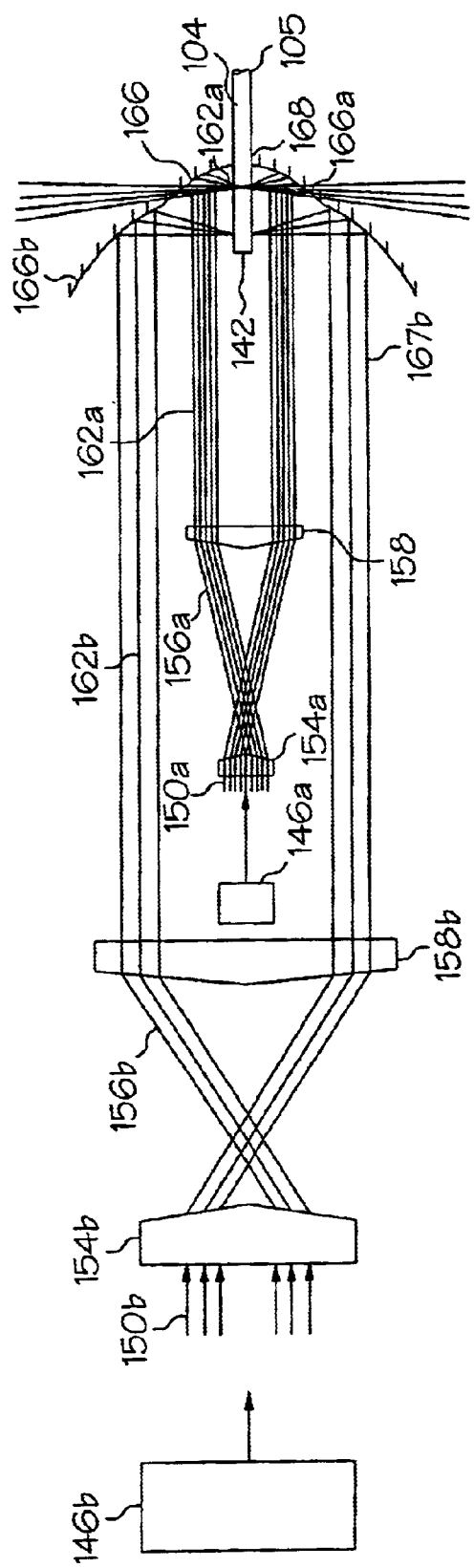
FIG. 13 is a schematic view of another apparatus that may be employed in the inventive process.

Simultaneously bonding multiple portions of a catheter may also be accomplished using suitable beam splitting techniques to split an initial energy beam into two beams and then focusing each of the beams into an annular beam. Simultaneous bonding may also be accomplished by using two or more laser sources as shown, for example, in FIG. 13. As shown in FIG. 13, two laser sources 146a,b are provided.

First laser source 146a generates a first beam 150a which is conditioned with two conical lenses 154a and 158a to form annular beam 162a. Similarly, second laser source 146b generates a second beam 150b which is conditioned with two conical lenses 154b and 158b to form annular beam 162b. Annular beams 162a,b are reflected inward by parabolic mirror 166. Parabolic mirror 166 is a bifocal parabolic mirror comprising a smaller focal length portion 166a and a larger focal length portion 166b. Reflected beams 167a,b impinge on catheter 168 at two locations along catheter 168. The arrangement of the optics is similar to that of FIG. 3 with two lasers and optical systems rather than one.

The other single beam embodiments disclosed herein may similarly be modified for use in simultaneously bonding.

Figure 14:
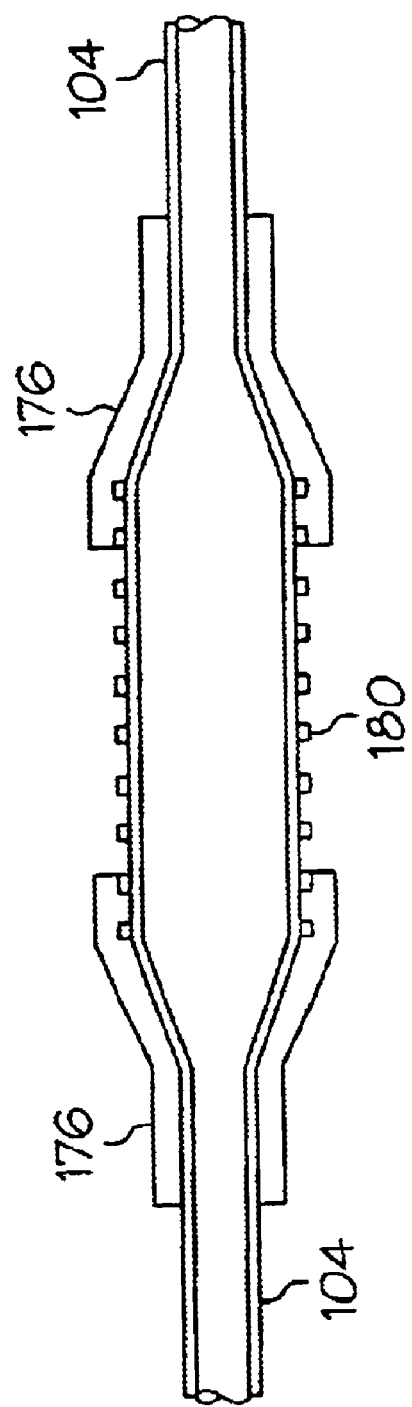
FIG. 14 is a schematic sectional side view of a catheter tube having a stent and retention sleeves disposed thereon.

The invention has been described above with respect to bonding a polymeric balloon material to a tubular body such as a catheter. The invention is also directed to a method of bonding a retention sleeve (such as for stents and grafts or other medical devices) or any other suitable polymeric material to a catheter tube. As shown in FIG. 14, retention sleeve 176 is fusion bonded to catheter tube 104. Retention sleeve 176 retains stent 180 on catheter tube 104. The bond is achieved using the apparatuses disclosed herein by directing the energy at the retention sleeve in the desired bond region. The retention sleeve may be made from elastic and compliant balloon materials, including materials disclosed in U.S. Pat. No. 6,068,634. Desirably, the retention sleeve will be made of a material which is radiopaque, at least in part.

As with the fusion bonding of a balloon, the retention sleeve must be suitably aligned about the desired portion of the catheter. The retention sleeve must also be suitably aligned about the stent. Optionally, as with balloons, heat shrink tubing made be disposed about the retention sleeve prior to fusion bonding. A beam of energy, as discussed above with respect to balloons, is then directed at the region of the desired bond to bond the retention sleeve to the catheter tube.

The retention sleeve may be made of suitable polymeric materials including the balloon materials disclosed above. Other suitable materials as well as other details concerning retention sleeves may be found in U.S. applications Ser. Nos. 09/407836 and 09/427805.

The inventive processes may also be used to bond together two catheter tubes or a catheter tube and a sheath. An example of a catheter having a retractable sheath and a dual lumen tube is provided in U.S. Pat No. 5,957,930. The retractable sheath disclosed therein may be bonded to the dual lumen tube using the inventive methods disclosed herein. The particular choice of energy wavelength will depend on the particular materials used for the dual lumen tube. Other portions of the catheter which may be bonded together using the inventive methods include the slide sheath and the outer shaft, the bumpers and the catheter shaft, the sliding seal and the outer shaft and the manifold and a hypotube. More generally, those polymeric portions of a catheter which are currently bonded together using other techniques may be amenable to the inventive methods.

The invention is also directed more generally to a process for sealing a polymeric material to a polymeric catheter tube. The process comprises the steps of selecting at least one wavelength of energy that is at least partially absorbed by at least one of the polymeric material and the polymeric catheter tube, generating at least one annular beam of electromagnetic energy at said selected energy wavelength, controllably directing the annular beam of energy onto the polymeric material to concentrate the energy in a bond site circumscribing the catheter tube to at least partially melt at least one material selected from the group consisting of the polymeric material and the polymeric catheter tube along the bond site and the immediate region thereof and allowing at least one partially melted polymeric material to cool and solidify to form a fusion bond between the tube and the polymeric material.

The invention is also directed to processes for bonding polymeric materials to catheter tubes continuously about the periphery of the catheter tube. The polymeric material may itself be in the form of a tube or may be in the form of a sheet wrapped around the periphery of the catheter.

Other uses for the inventive processes include bonding polymeric sheaths to catheter tubes, bonding sheet-like or tubular balloon protectors to balloons or catheter tubes and bonding a catheter tip to a catheter. As with the bonding of balloons to catheters, an annular beam of energy is directed at the polymeric material and catheter in the desired bonding region.

The invention is also directed to bonding polymeric materials to medical balloons. For example, in the case of a catheter carrying a balloon expandable stent, a flexible sheath may be bonded to the medical balloon about the periphery of the balloon in order to protect the balloon from any edges on the stent.

In another embodiment, the invention is directed to a process for forming a fluid tight seal between a polymeric body and a polymeric member surrounding the body. The process comprises the steps of positioning a polymeric member along and in surrounding relation to a body of polymeric material, with the polymeric member and body aligned to place a first surface portion of the polymeric member and a second surface portion of the body in a contiguous and confronting relation. The polymeric materials forming the body and the polymeric member have non-uniform energy absorption spectra that include high absorptivity wavelength bands. At least one of the high absorptivity wavelength bands of the polymeric material forming the body and at least one of the high absorptivity wavelength bands of the polymeric member overlap one another in at least one range of overlapping wavelengths. A monochromatic energy wavelength that is contained within at least one of the overlapping wavelength ranges is selected. An annular beam of substantially monochromatic electromagnetic energy is generated at the selected monochromatic energy wavelength and controllably directed onto the body and the polymeric member to concentrate the monochromatic energy in a narrow bond site circumscribing the body and running along the interface of the first and second surface portions. The beam melts the polymeric materials along the bond site and the immediate region thereof. Finally, the previously melted polymeric material is allowed to cool and solidify to form a fusion bond between the body and polymeric member.

Desirably, the polymeric member is a dilatation member and the polymeric body is a catheter tube. Also desirably, the dilatation member is a catheter balloon positioned along a distal end region of the catheter tubing a includes proximal and distal neck portions, a medial region having a diameter substantially larger than that of the neck portions, and proximal and distal tapered conical regions between the medial region and respective neck regions.

In another embodiment, the invention is directed to a process for simultaneously bonding at least two polymeric materials to a catheter tube. The process comprises the steps of providing a catheter tube having at least a first predetermined bonding location and a second predetermined bonding location for bonding a polymeric material thereto, each bonding location having a polymeric material circumscribing the catheter tube at the bonding location. A first annular beam of electromagnetic energy that is at least partially absorbed by the polymeric material at the first bonding location and a second annular beam of electromagnetic energy that is at least partially absorbed by the polymeric material at the second bonding location are simultaneously generated. The first and second annular beams of energy are controllably directed onto the polymeric balloon material at the first and second predetermined bonding locations to concentrate the energy into the first and second predetermined bond sites circumscribing the catheter tube and to at least partially melt the polymeric balloon material along the bond sites and the immediate regions thereof. The previously melted polymeric materials in the first and second bonding locations are allowed to solidify to form fusion bonds between the catheter tube and the polymeric material at the first and second bonding locations.

In a further embodiment, the invention is directed to a process for simultaneously welding the proximal and distal ends of a balloon to a catheter tube. In accordance with the inventive process, at least one wavelength of energy that is at least partially absorbed by the balloon is selected and a first annular beam of electromagnetic energy generated at the selected energy wavelength and a second annular beam of electromagnetic energy generated at the selected energy wavelength. The first annular beam is controllably directed toward the proximal end of the balloon to concentrate the energy in a narrow bond site circumscribing the catheter tube and running along the interface of the first and second surface portions, thus to melt the polymeric materials along the bond site and the immediate region thereof. The previously melted polymeric material is allowed to cool and solidify to form a fusion bond between the catheter tube and the balloon. The second annular beam is controllably directed toward the distal end of the balloon to concentrate the energy in a narrow bond site circumscribing the catheter tube and running along the interface of the first and second surface portions, thus to melt the polymeric materials along the bond site and the immediate region thereof. The previously melted polymeric material at the distal end is allowed to cool and solidify to form a fusion bond between the catheter tube and the distal end of the balloon.

The frequency of the energy which is directed at the polymeric material in the inventive processes may be chosen such that the energy is at least partially absorbed by the balloon, by the polymeric catheter tube or by both the balloon and polymeric catheter tube. The energy should be supplied at a sufficient power level as to cause at least one of and preferably both of the balloon and polymeric catheter tube to at least partially melt in the region of the desired bond.

Thus far, the energy has been described as monochromatic. The invention also contemplates the use of non-monochromatic energy as long as the energy is properly focused and of sufficient intensity to cause melting of the polymeric material to which it is directed. As such, multiple frequencies of energy may be employed as long as the energy contains one or more frequencies which are strongly absorbed by at least one of the polymeric materials. Desirably, substantially all of the frequencies of energy will be strongly absorbed by at least one of the polymeric materials.

The inventive processes may also be used to bond together multiple layers of polymeric materials. For example, the inventive processes may be used to simultaneously bond a stent retention sleeve to a balloon and the balloon to a catheter. This would, of course, require proper alignment of the balloon, retention sleeve and catheter. Also desirably, the balloon, retention sleeve and catheter will all strongly absorb energy of same wavelength or will all have overlapping absorption bands.

The invention may also be used to join together tubular members that have a non-circular cross-section. Thus, for example, the inventive processes may be used to bond a balloon to a tube with an elliptical cross-section. In order to achieve substantially uniform heating about the elliptical periphery of the balloon or other tube, it is desirable to substitute the parabolic reflecting mirror with a mirror with a cross-section which is the same shape as the tube to be processed. It will be readily recognized that through the use of suitable lenses and reflecting mirrors, substantially uniform beating of tubes with other cross-sectional shapes may be achieved as well.

Figure 15B:
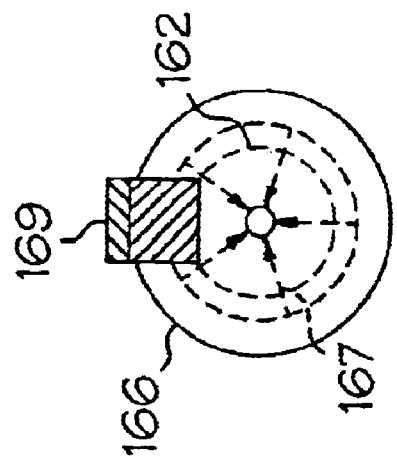
Figure 15A:
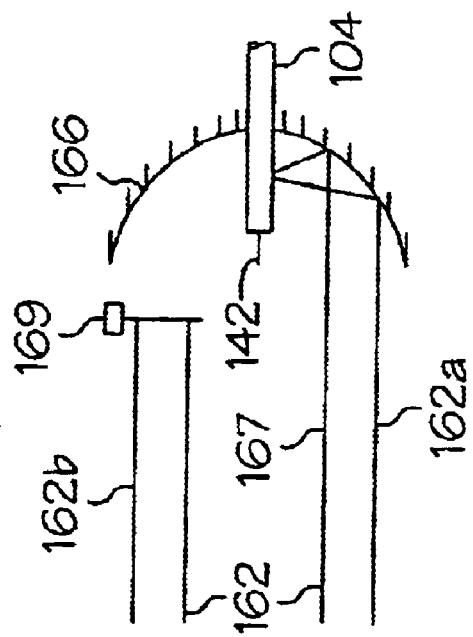
FIG. 15a is a schematic sectional side view of a portion another apparatus that may be employed in the inventive process.

The invention is also directed to a process for selectively welding or bonding a material to a portion of the circumference or periphery of a catheter or other tube. As shown in FIGS. 15a and 15b, an annular laser beam 162 is generated and a portion of the beam blocked via beam block 169. Portion 162a of beam 162 reflects off of parabolic mirror 166 and onto catheter 104. Portion 162b of beam 162 is blocked. Annular beam 162 may be generated using any of the apparatuses disclosed above. Where the beam is generated using a conical lens (not shown), beam block 162 may be placed in between the conical lens and the parabolic reflector 166. The beam block may also be placed elsewhere. For example, a beam block may be placed between the parabolic reflector and the catheter. The beam block may be any suitable material to block a portion of the annular laser beam. A beam block may also be implemented by altering and/or destroying the reflective properties of a desired portion of the parabolic reflector. Similarly, an annular beam with a portion or segment blocked or absent may be created by a modified conical lens or HOE. By blocking a portion of the beam or providing a beam with a segment absentia weld or bond which extends only part of the way around the catheter may be achieved.

Selectively welding only a portion of the circumference or periphery of the catheter may prove beneficial in catheter formation, such as in the region of the port bond where a guidewire enters a catheter in mid-section on monorail catheters.

The invention may also be practiced by moving the catheter axially during the application of laser energy. This allows for additional control of the amount of energy delivered to the bonding site. When movement of the catheter is slow, more power is delivered to the bonding site. When movement of the catheter is fast, less power is delivered to the bonding site. Moreover, in this way, a longer weld or bond may be achieved. This may prove particularly useful in welding a soft tip onto the end of a catheter tube where, typically, weld lengths are from about 2 mm to about 55 mm in length. When the catheter is moved along the optical axis during welding, the focussed annular beam effectively moves along the catheter thereby creating a continuous bond or weld of desired length. The same effect may also be achieved by moving the parabolic mirror or the focussing lens.

Varying the movement speed of the catheter or parabolic mirror may also be beneficial where the thickness of the materials to be welded varies along the length of the region to be welded. Where a thicker region is encountered, the rate of movement of the catheter may be slowed down to apply more energy thereto. Where a thinner region is encountered, the rate may be increased as less energy is needed to heat the material.

Finally, the invention is directed to the novel apparatuses disclosed herein, including those apparatuses made using the inventive processes disclosed herein.

In addition to the specific embodiments claimed below, the invention is also directed to other embodiments having any other possible combination of the dependent features claimed below.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A process for sealing at least one polymeric material to a Polymeric catheter tube, comprising the steps of:

providing a catheter tube having a first predetermined bonding location and a second predetermined bonding location for bonding a polymeric material thereto, each bonding location separate from each other and having a polymeric material overlapping the catheter tube at the bonding location;

simultaneously generating a first and a second annular bean of electromagnetic energy from two separate energy sources, the first beam being at least partially absorbable at a selected energy wavelength by at least one of the polymeric material at the first bond site location and the catheter tube and the second beam being at least partially absorbable at a selected energy wavelength by at lent one of the polymeric material at the second bond site location and the polymeric catheter tube;

controllably directing the first annular beam of electromagnetic energy by redirecting the first beam with a parabolic mirror onto the polymeric material to concentrate the energy in the first bond site location so as to at least partially melt at least one material selected from the group consisting of the polymeric material and the polymeric catheter tube along the first bond site location and immediate regions thereof;

and controllably directing the second annular beam of electromagnetic energy by redirecting the first beam with a parabolic mirror onto the polymeric material to concentrate the energy in the second bond site location so as to at least partially melt at least one material selected from the group consisting of the polymeric material and the polymeric catheter tube along the second bond site location and immediate region thereof; and allowing the at least two partially melted materials to cool and solidify to form a fusion bond between the polymeric catheter tube and the polymeric material.

2. The process of claim 1 wherein the polymeric material is a polymeric balloon material.

3. The process of claim 2 wherein the energy is substantially monochromatic.

4. The process of claim 2 wherein the energy is not substantially monochromatic.

5. The process of claim 2 wherein the energy is at least partially absorbed by the polymeric balloon material and the polymeric catheter tube.

6. The process of claim 2 wherein at least two annular of electromagnetic energy are generated.

7. The process of claim 6, the polymeric balloon material having a proximal end and a distal end, wherein a first annular beam is directed at the proximal end of the polymeric balloon material and a second beam is directed at the distal end of the polymeric balloon material.

8. The process of claim 7 wherein the first annular beam is directed to the proximal end of the polymeric balloon material at the same time that the second beam is directed to the distal end of the polymeric balloon material.

9. The process of claim 2 wherein the polymeric material is formed from the polymer selected from the group consisting of: polyester, polyolefins, polyamides, thermoplastic polyurethanes and their copolymers, polyethylene terephthalate, nylon, and combinations thereof.

10. The process of claim 2 wherein the energy is at least partially absorbed by the polymeric balloon material causing the polymeric balloon material to at least partially melt.

11. The process of claim 2 wherein the energy is at least partially absorbed by the polymeric catheter tube causing the polymeric catheter tube to at least partially melt.

12. The press of claim 2 wherein the energy is at least partially absorbed by the polymeric catheter tube causing the polymeric catheter tube to at least partially melt and by the polymeric balloon material causing the polymeric balloon material to at least partially melt.

13. The process of claim 1 wherein the polymeric material is a retention sleeve.

14. The process of claim 1 wherein the annular beam is not substantially circular.

15. The process of claim 1 wherein after being generated the annular beam is redirected by passing through a lens.

16. The process of claim 1 wherein each annular beam is generated and directed through the use of a lens.

17. The process of claim 16 wherein each annular beam is generated and directed through the use of two lenses.

18. The process of claim 1 wherein a portion of the annular beam is blocked.

19. A process for bonding at least one polymeric material to a polymeric catheter tube having a longitudinal axis extending beyond each end of the polymeric catheter tube, comprising the steps of:

over-lapping a portion of the at least one polymeric material with a portion of the polymeric catheter tube thereby creating an over-lapped portion;

generating an annular beam of electromagnetic energy such that the annular beam is disposed about the longitudinal axis of the polymeric catheter tube without impinging on the polymeric material or the polymeric catheter tube, the electromagnetic energy at least partially absorbable by at least one of the polymeric material and the polymeric catheter tube at a selected energy wavelength;

controllably redirecting at least a portion of the annular beam of electromagnetic energy such that it converges onto the polymeric material at the over-lapped portion circumscribing at least a portion of the polymeric catheter tube to at least partially melt at least one material selected from the group consisting of the polymeric material and the polymeric catheter tube along at least a portion of the overlapped portion.

20. The process of claim 19, wherein there is a plurality of annular beams, each annular beam to be directed to the overlapped portion is substantially disposed about the longitudinal axis of the catheter tube.

21. The process of claim 19, wherein the polymeric catheter tube in the region of the overlapped portion has a circular cross-section.

* * * * *

UNITED STATES PATENT AND TRADEMARK OFFICE
CERTIFICATE OF CORRECTION

PATENT NO.    : 6,860,960 B1
DATED         : March 1, 2005
INVENTOR(S)   : Aiden Flangan It is certified that error appears in the above-identified patent and that said Letters Patent is hereby corrected as shown below:

Column 4,
Line 32, after "of", insert -- a --.
Line 59, after last word "portion" insert -- of --.

Column 5,
Line 15, after "thermoplastic", delete "in".
Line 46, after "from", delete "made from".
Line 52, change "Arnitel", to -- Arnitel ® --.
Line 52, change "Hytrel" to -- Hytrel ® --.

Column 7,
Line 1, after "and", insert -- are --.
Line 62, last word "my" change to -- may --.

Column 8,
Line 50, after "of", insert -- the --.
Line 51, before last word "distal", insert -- the --.
Line 64, after "absorptivity", insert -- of --.

Column 9,
Lines 23 & 24, change "overlap-pings" to -- overlap-ping --.
Line 31, after first word "include", delete "a".
Line 31, after "hyperbolic", change "mirror" to -- mirrors --.
Line 38, after "invention" change "fuller" to -- further --.
Line 47, after "hologram" insert -- , --.

Column 10,
Line 34, after "tubing" change "made" to -- may --.

Column 11,
Line 60, after "tubing", change "a" to -- and --.

Column 13,
Line 40, after "segment", change "absentia" to -- absent, a --.
Line 60, after "the", change "focussed" to -- focused --.
Line 63, after "the", change "focussing" to -- focusing --.

UNITED STATES PATENT AND TRADEMARK OFFICE
CERTIFICATE OF CORRECTION

PATENT NO.    : 6,860,960 B1
DATED         : March 1, 2005
INVENTOR(S)   : Aiden Flangan It is certified that error appears in the above-identified patent and that said Letters Patent is hereby corrected as shown below:

Column 14,
Line 13, after "above", change "Examples" to -- examples --.
Line 24, before "catheter", change "Polymeric" to -- polymeric --.
Line 33, first word "bean", change to -- beam --.
Line 39, before "one", change "lent" to -- least --.

Column 15,
Line 4, after "annular", insert -- beams --.
Line 26, after "the" (first occurrence), change "press" to -- process --.

Column 16,
Line 32, first word "overlapped", change to -- over-lapped --.
Line 35, before "portion", change "overlapped" to -- over-lapped --.

Signed and Sealed this

Ninth Day of August, 2005

JON W. DUDAS
*Director of the United States Patent and Trademark Office*